United States Patent [19]
Kodama et al.

[11] Patent Number: 5,900,488
[45] Date of Patent: May 4, 1999

[54] METHOD FOR TREATING MYCOSIS USING IMIDAZOLYLACETONITRILE DERIVATIVES

[75] Inventors: Hiroki Kodama; Yoshimi Niwano; Kazuo Kanai, all of Osaka; Masanori Yoshida, Wakayama, all of Japan

[73] Assignee: Nihon Nohyaku Co., Ltd., Tokyo, Japan

[21] Appl. No.: 08/981,420

[22] PCT Filed: Jul. 5, 1996

[86] PCT No.: PCT/JP96/01872

§ 371 Date: Dec. 31, 1997

§ 102(e) Date: Dec. 31, 1997

[87] PCT Pub. No.: WO97/02821

PCT Pub. Date: Jan. 30, 1997

[30] Foreign Application Priority Data

Jul. 8, 1995 [JP] Japan .................................. 7-196174

[51] Int. Cl.$^6$ ...................... A61K 31/415; C07D 239/00; C07D 409/06; C07D 233/00
[52] U.S. Cl. ......................... 548/315.1; 514/397
[58] Field of Search ................. 548/315.1, 397

[56] References Cited

U.S. PATENT DOCUMENTS 4,636,519  1/1987  Seo et al. ................................ 514/397

FOREIGN PATENT DOCUMENTS 2-275877  11/1990  Japan .................................. 548/315.1
5-271226  10/1993  Japan .................................. 548/315.1

OTHER PUBLICATIONS

Database WPI, Week 9051, Derwent Publications Ltd., London, GB & JP, A, 02 275 877 (Nihon Noyaku KK), 9 Nov. 1990.

Arzneimittelforschung, vol. 42, No. 3, 1992, pp. 345–349, H. Oka et al.: "Therapeutic Efficacy of Latoconazole in Formulations of Clinical Use on Experimental Dermatophytosis in Guinea Pigs."

Antimicrob. Agents Chemother., vol. 38, No. 9, 1994, pp. 2204–2206, Y. Niwano et al.: "Therapeutic Efficacy of Latoconazole, a New Imidazole Antimycotic Agent, for Experimental Cutaneous Candidiasis in Guinea Pigs."

Arzneimittelforschung, vol. 41, No. 8, 1991, pp. 847–851, T. Ohmi et al.: "Antifungal Activity of the new Agent Latoconazole in Two Tinea Models."

*Primary Examiner*—Floyd D. Higel
*Attorney, Agent, or Firm*—Sughrue, Mion, Zinn Macpeak & Seas, PLLC

[57] ABSTRACT

R-(+)-(E)-[4-(2-Chlorophenyl)-1,3-dithiolan-2-ylidene]-1-imidazolylacetonitrile, R-(−)-(E)-[4-(2,4-dichlorophenyl)-1,3-dithiolan-2-ylidene]-1-imidazolylacetonitrile, and pharmaceutically acceptable salts thereof which can be used as a pharmaceutical agent are disclosed. A process for producing them and a method for treating mycoses using them are also disclosed.

4 Claims, No Drawings

METHOD FOR TREATING MYCOSIS USING IMIDAZOLYLACETONITRILE DERIVATIVES

This is a National Stage filing under 35 U.S.C. §371 of PCT/JP96/018725, filed Jul. 5, 1996.

TECHNICAL FIELD

The present invention relates to an antifungal agent, a method for preventing or treating mycoses using the antifungal agent, a novel optically active derivative and a salt thereof, and a process for producing the derivative.

BACKGROUND ART

Various azole compounds having antifungal activity have been known. For example, JP-A-60-218387 discloses imidazole compounds represented by the following formula (a) (the term "JP-A" as used herein means an "unexamined published Japanese patent application"):

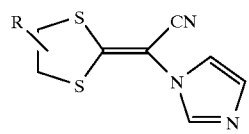

(a)

Moreover, JP-A-62-93227 discloses that these compounds are useful as an antifungal agent. Furthermore, JP-A-2-275877 discloses that the optically active compounds of specific compounds among the above imidazole compounds have antifungal activity against *Trichophyton mentagrophytes* about 1.4 times the activity of racemic compounds thereof.

DISCLOSURE OF THE INVENTION

An object of the present invention is to provide antifungal agents comprising optically active compounds having more excellent antifungal activity than racemic compounds thereof.

Another object of the present invention is to provide the optically active compounds, a process for producing them, and a method for using them.

These and other objects of the present invention have been attained by a pharmaceutical composition comprising as an active ingredient R-(+)-(E)-[4-(2-chlorophenyl)-1,3-dithiolan-2-ylidene]-1-imidazolylacetonitrile (hereinafter referred to as "Compound (A)") or R-(−)-(E)-[4-(2,4-dichlorophenyl)-1,3-dithiolan-2-ylidene]-1-imidazolylacetonitrile (hereinafter referred to as "Compound (B)") represented by the following formula (I):

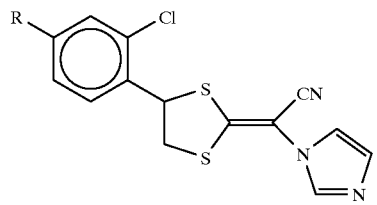

(I)

wherein R represents a hydrogen atom or a chlorine atom, or a pharmaceutically acceptable salt thereof; together with a pharmaceutically acceptable carrier or diluent.

Furthermore, these and other objects of the present invention have been attained by Compound (B) or a salt thereof.

Moreover, these and other objects of the present invention have been attained by a process for producing Compound (B) which comprises reacting an optically active glycol derivative represented by the following formula (II) or an equivalent thereof with a compound represented by the following formula (III):

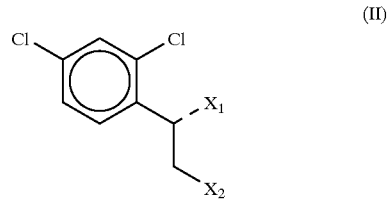

(II)

wherein $X_1$ and $X_2$ are the same or different and each represents a methanesulfonyloxy group, a benzenesulfonyloxy group, a p-toluenesulfonyloxy group, or a halogen atom:

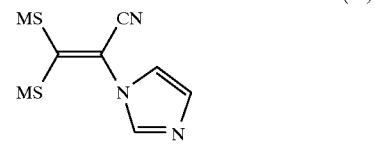

(III)

wherein M represents an alkali metal atom.

Still furthermore, these and other objects of the present invention have been attained by a method for preventing or treating mycosis which comprises administering to human or animals in need of such prevention or treatment a pharmaceutically effective amount of Compound (A) or Compound (B), or a pharmaceutical acceptable salt thereof; optionally together with a pharmaceutical acceptable carrier or diluent.

Still moreover, these and other objects of the present invention have been attained by use of Compound (A) or Compound (B), or a pharmaceutically acceptable salt thereof for preparing a pharmaceutical composition.

BEST MODE FOR PRACTICING INVENTION

Specifically, Compounds (A) and (B) are shown below.

Compound (A):

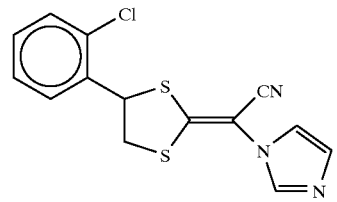

Compound (B):

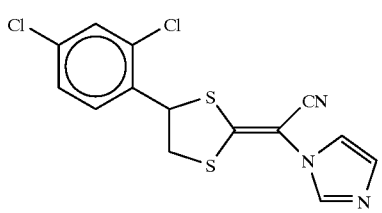

The present inventors have found that Compound (A) or Compound (B) represented by formula (I) and pharmaceutically acceptable salts thereof, namely, (R)-enantiomers, have antifungal activity several times that of racemic mixtures thereof against dermatophytes, especially highly sensitive strains, and that Compound (B) which has not been described in any literatures and is a novel compound has superior antifungal activity unexpectable from the racemic mixtures thereof. Thus, the present invention has been accomplished.

Compounds (A) and (B) are highly sensitive to, especially, *Trichophyton rubrum*. The antifungal activity thereof is 2 to 4 times as high as that of the racemic mixtures thereof.

Compound (A) can be produced, for example, by the process disclosed in JP-A-2-275877. Compound (B) can be produced by the process illustrated below.

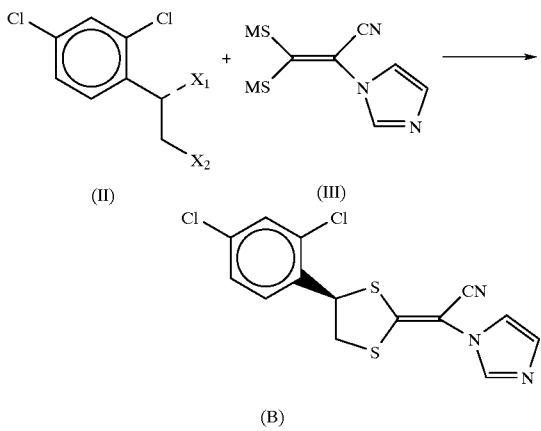

In formula, $X_1$ and $X_2$ are the same or different and each represents a methanesulfonyloxy group, a benzenesulfonyloxy group, a p-toluenesulfonyloxy group or a halogen atom; and M represents an alkali metal atom. Examples of the halogen atom represented by $X_1$ or $X_2$ include a fluorine atom, a chlorine atom, a bromine atom and an iodine atom. Examples of the alkali metal atom represented by M include Li, Na and K.

That is, in the same manner as described in JP-A-2-275877, Compound (B) can be produced by reacting an optically active glycol derivative having a configuration of (S) represented by formula (II) or an equivalent thereof with a dithiolate salt represented by formula (III).

The dithiolate salt represented by formula (III) can be produced by reacting 1-cyanomethylimidazole shown below with carbon disulfide in the presence of a base and an inert solvent.

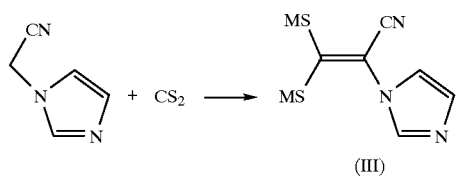

In formula, M is the same as defined above.

Any inert solvents can be used in the above reaction as far as they do not inhibit the progress of the reaction. Examples thereof include alcohols (e.g. , methanol, ethanol, isopropanol), polar solvents (e.g. , dimethyl sulf oxide (DMSO), dimethylformamide, acetonitrile), water, and mixed solvents thereof.

Examples of the base include sodium carbonate, potassium carbonate, sodium hydroxide and potassium hydroxide. They can be used as they are in the form of solid or as a solution in an inert solvent. Amount (mol) of the base can be selected from the range of 2 to 8 times, preferably 4 to 6 times, the amount (mol) of 1-cyanomethylimidazole.

The compound represented by formula (II) can be used in an amount equimolar to or in excess of 1-cyanomethylimidazole.

The reaction temperature can be selected from the range of 0 to 100° C., and is preferably about room temperature. The reaction time can be selected from the range of 0.5 to 24 hours.

The resulting compound is a mixture of geometrical isomers E and Z, and the desired E-isomer represented by formula (I) can be isolated and purified by, e.g., silica gel column chromatography, fractional crystallization. Examples of solvents for purification by fractional crystallization and recrystallization include ethanol, ethyl acetate, ether, hexane, acetone, and mixed solvents thereof, but these are not limitative.

The optically active starting compounds represented by formula (II) can be produced by known processes 1 to 3 illustrated below.

Process 1:

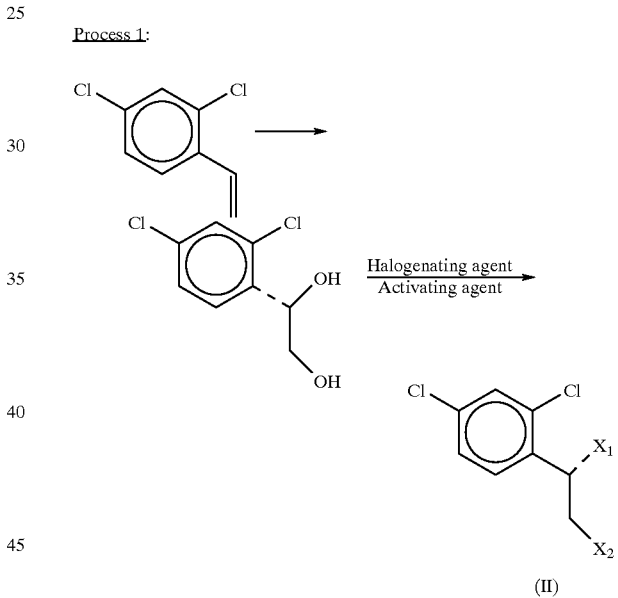

In formula, $X_1$ and $X_2$ are the same as defined above.

That is, they can be produced by reacting (S)-1-(2,4-dichlorophenyl)ethane-1,2-diol obtainable from 2,4-dichlorostyrene by a known process [*J. Org. Chem. Soc.*, 57:2768 (1992)] with a suitable halogenating agent (e.g., thionyl chloride, phosphorus tribromide, carbon tetrachloride/triphenylphosphine) or an activating agent (e.g., methanesulfonyl chloride, toluenesulfonyl chloride, benzenesulfonyl chloride).

Process 2:

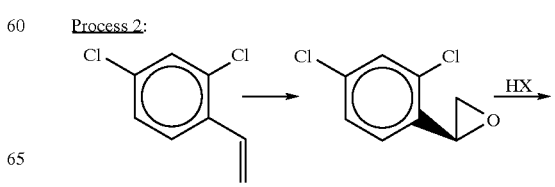

-continued

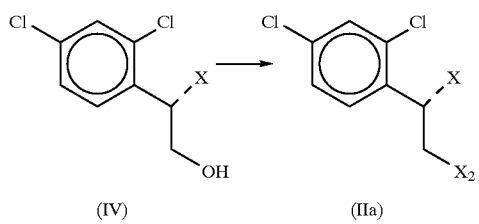

(IV)  (IIa)

In formula, X represents a chlorine atom or a bromine atom; and $X_2$ is the same as defined above.

As illustrated above, the compounds represented by formula (II) in which $X_1$ is a chlorine atom or a bromine atom (i.e. the compounds represented by formula (IIa)) can be, produced by reacting (R)-1-(2,4-dichlorophenyl)styrene oxide obtainable from 2,4-dichlorostyrene by a known process [*J. Am. Chem. Soc.*, 113:7063 (1991)] with a hydrogen halide to prepare a haloalcohol represented by formula (IV), and then reacting the haloalcohol with a suitable halogenating agent (e.g., thionyl chloride, phosphorus tribromide, carbon tetrachloride/triphenylphosphine) or an activating agent (e.g., methanesulfonyl chloride, toluenesulfonyl chloride, benzenesulfonyl chloride).

Process 3:

The compounds represented by formula (II) in which $X_2$ is a chlorine or bromine atom (i.e., the compounds represented by formula (IIb)) can be produced by process 3 shown below.

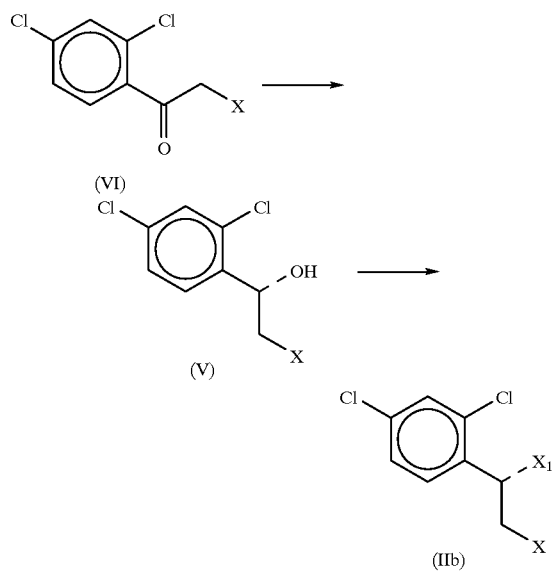

In formula, X represents a chlorine atom or a bromine atom; and $X_1$ is the same as defined above.

That is, the desired compounds can be obtained by reacting a haloalcohol represented by formula (V) which can be synthesized from a 2,4-dichlorophenacyl halide by a known process [*Modern Synthetic Methods*, 5:115 (1989)] with a suitable halogenating agent (e.g., thionyl chloride, phosphorus tribromide, carbon tetrachloride/triphenylphosphine) or an activating agent (e.g., methanesulfonyl chloride, toluenesulfonyl chloride, benzenesulfonyl chloride).

The compositions of the present invention are antifungal agents useful for curing mycotic infection of human or animals. For example, these can be used for curing local mycotic infection, mucosa mycotic infection, generalized mycotic infection caused by, e.g., fungi of the genera Trichophyton, Candida, and Aspergillus.

Compound (A), Compound (B) and a pharmaceutically acceptable salt thereof are each used alone or in the form of a composition comprising the compound and a pharmaceutically acceptable carrier or diluent. They are formed into preparations suitable for oral or non-oral administration, such as liquid formulation, tablet, emulsion, ointment, cream, lotion, and poultice.

The amount administered can be any convenient amount according to age, body weight, and administration form, but is normally at least 0.05 mg, preferably from 0.5 to 50 mg, per 1 kg of body weight and per one day for general treatment of adults and the agent can be administered at one time or several times in parts in one day.

In the case of local treatment, for example, in the form of topical application, the concentration of the active ingredient is preferably at least 0.001%, more preferably from 0.1 to 2%. The amount of treatment is preferably from 30 to 100 mg per $cm^2$.

The antifungal agent of the present invention may be used in admixture with other antifungal agents or antibacterial agents such as amphotericin B, trichomycin, varitotin, and clotrimazole.

EXAMPLE

The present invention will now be illustrated in greater detail with reference to the following Examples, Reference Examples, Formulation Examples, and Test Examples, but it should be understood that the invention is not construed as being limited thereto. Unless otherwise indicated, all the percents are by weight.

Example 1

Preparation of Compound (B) by Process 3:

1-(a). Preparation of (S)-1-(2,4-dichlorophenyl)-2-bromoethanol:

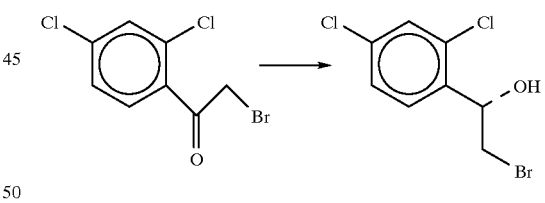

To 5 ml of dry tetrahydrofuran (THF) was added 300 mg of (S)-3,3-diphenyl-1-methyltetrahydro-1H,3H-pyrrolo-[1,2-c][1,3,2]oxazaborole, and then thereto was added dropwise 8 ml of 1.0M borane-THF solution at −20° C. At the same temperature, thereto was further added dropwise a solution of 2.7 g of 2.4-dichlorophenacyl bromide in 8 ml of THF. The resultant mixture was heated to room temperature, and then stirred for 3 hours. Next, 10 ml of methanol was added to decompose excess borane, and then the reaction mixture was poured into water and extracted with ether. The organic layer was washed with water and dried over anhydrous magnesium sulfate. The solvent was distilled off under reduced pressure and the residue was purified by silica gel column chromatography (ethyl acetate/n-hexane=⅓) to obtain 2.5 g of the desired product at an optical purity of 80% ee.

1-(b). Preparation of (S)-[1-(2,4-dichlorophenyl)-2-bromoethyl]methanesulfonate:

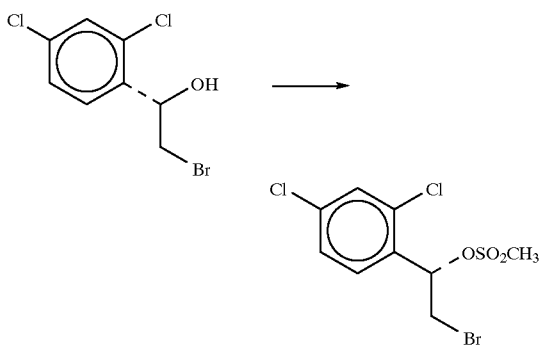

In 30 ml of methylene chloride was dissolved 1.6 g of (S)-1-(2,4-dichlorophenyl)-2-bromoethanol, and then 660 mg of triethylamine was added to the solution. Next, 750 mg of methanesulfonyl chloride was further added dropwise thereto under ice cooling. One hour after stirring at room temperature, the reaction mixture was washed with water and dried over anhydrous magnesium sulfate. The solvent was distilled off under reduced pressure to obtain 1.9 g of a crude product of the desired compound. The resulting crude product was used for the next reaction without purification.

1-(c). Preparation of (R)-(−)-(E)-[4-(2,4-dichlorophenyl)-1,3-dithiolan-2-ylidene]-1-imidazolylacetonitrile (Compound (B)):

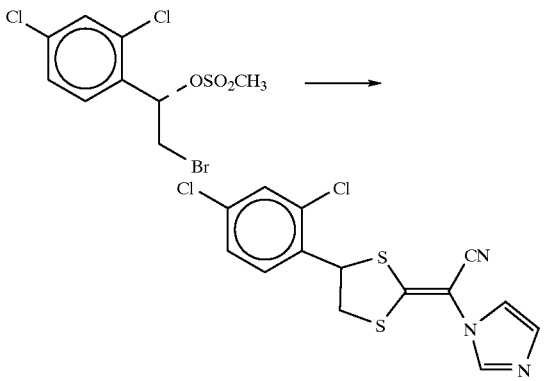

To 10 ml of DMSO was added 440 mg of potassium hydroxide, and, under cooling in a water bath, thereto was added dropwise a solution prepared by dissolving 300 mg of 1-cyanomethylimidazole and 210 mg of carbon disulfide in 5 ml of DMSO, followed by stirring for 1 hour at room temperature to prepare a dithiolate solution. Then, the resulting dithiolate solution was added dropwise to a solution prepared by dissolving 950 mg of the crude product of (S)-1-[2,4-dichlorophenyl)-2-bromoethyl]methanesulfonate in 10 ml of DMSO under cooling in a water bath. Two hours after stirring at room temperature, the reaction mixture was poured into ice water and extracted with ethyl acetate. The organic layer was washed with water, and then dried over anhydrous magnesium sulfate. Next, the solvent was distilled off under reduced pressure. The residue was purified by silica gel column chromatography (ethyl acetate (AcOEt)/n-hexane=2/1). The resulting crystal was recrystallized from a mixed solvent of ethyl acetate-n-hexane to obtain 350 mg of the desired product at an optical purity of 95% ee.

Example 2

Preparation of Compound (B) by Process 1:

2-(a). Preparation of (S)-1-(2,4-dichlorophenyl)-ethane-1,2-bismethanesulfonate:

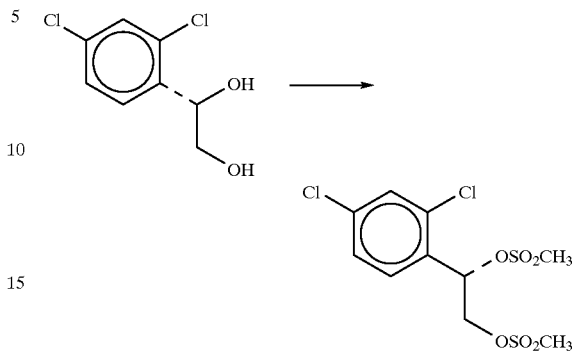

(S)-1-(2,4-Dichlorophenyl)-1,2-ethanediol (1.5 g; optical purity 98% ee) synthesized by a known process [*J. Org. Chem.*, 57:2768 (1992)] and 3.1 g of triethylamine were dissolved in 50 ml of methylene chloride and 3.3 g of methanesulfonyl chloride was added dropwise to the solution under ice cooling. Two hours after stirring at room temperature, the reaction mixture was washed with water and the organic layer was dried over anhydrous magnesium sulfate. The solvent was distilled off under reduced pressure to obtain 2.6 g of a crude product of the desired compound. The resulting crude product was used for the next reaction without purification.

2-(b). Preparation of (R)-(−)-(E)-[4-(2,4-dichlorophenyl)-1,3-dithiolan-2-ylidene]-1-imidazolylacetonitrile (Compound (B)):

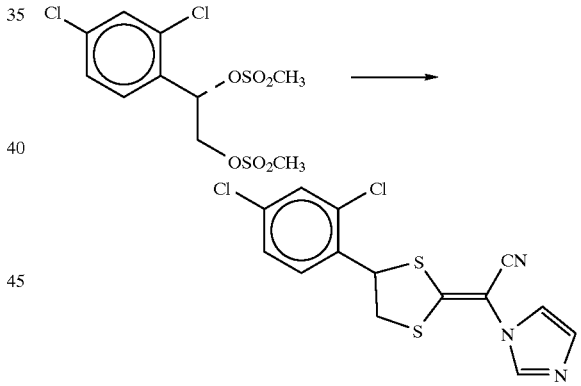

To 20 ml of DMSO was added 1.09 g of potassium hydroxide, and, under cooling in a water bath, thereto was added dropwise a solution prepared by dissolving 750 mg of 1-cyanomethylimidazole and 520 mg of carbon disulfide in 10 ml of DMSO, followed by stirring for 1 hour at room temperature to prepare a dithiolate solution. Then, under cooling in a water bath, the resulting dithiolate solution was added dropwise to a solution prepared by dissolving 2.61 g of the crude product of (S)-1-(2,4-dichlorophenyl)-ethane-1,2-bismethanesulfonate in 20 ml of DMSO. Two hours after stirring at room temperature, the reaction mixture was poured into ice water and extracted with ethyl acetate. The organic layer was washed with water and dried over anhydrous magnesium sulfate, and then the solvent was distilled off under reduced pressure. The residue was purified by silica gel column chromatography (AcOEt/n-hexane=2/1). The resulting crystal was recrystallized from a mixed solvent of ethyl acetate-n-hexane to obtain 1.2 g of the desired product at an optical purity of 99% ee. In the above examples, the optical purity was calculated from area percentage in HPLC using an optical active HPLC column (Chiralcel OD (trademark, Daicel Chemical Industry Ltd.)).

Reference Example 1

Preparation of (±)-(E)-[4-(2-chlorophenyl)-1,3-dithiolan-2-ylidene]-1-imidazolylacetonitrile:

Synthesis was carried out by the process described in Example 1 of JP-A-62-93227 to obtain a racemic compound having a melting point of 143.4° C. and a purity of 99.4%.

Reference Example 2

Preparation of R-(+)-(E)-[4-(2-chlorophenyl)-1,3-dithiolan-2-ylidene]-1-imidazolylacetonitrile (Compound (A)):

The racemic compound (100 g) obtained in Reference Example 1 was dissolved in 700 to 800 ml of acetone with heating to prepare a supersaturated solution. To this solution was added about 10 mg of a seed crystal of the optically active substance obtained by the process disclosed in JP-A-2-275877, followed by cooling to 25° C. and leaving for 4 to 15 hours, during which composition of the crystallized solution was analyzed by HPLC using an optical active column and the filtration point was determined. The precipitating crystals were collected by filtration and repeatedly subjected to the same procedure to obtain 25 g of R-enantiomer having an optical purity of 99.0% ee. In the above examples, the optical purity was calculated from area percentage in HPLC using an optical active HPLC column (Chiralcel ODR (trademark, Daicel Chemical Industry Ltd.)).

Formulation Example 1

| Compound (A) or (B) | 10 parts |
|---|---|
| Magnesium stearate | 10 parts |
| Lactose | 80 parts |

The above ingredients were uniformly mixed and the mixture was made into powders or fine particles to obtain a powder preparation.

Formulation Example 2

| Compound (A) or (B) | 50 parts |
|---|---|
| Starch | 10 parts |
| Lactose | 15 parts |
| Ethylcellulose | 20 parts |
| Polyvinyl alcohol | 5 parts |
| Water | 30 parts |

The above ingredients were uniformly mixed and kneaded, and then the mixture was ground. The resulting particles were sifted to obtain a granular preparation.

Formulation Example 3

| Compound (A) or (B) | 0.5 part |
|---|---|
| Nonionic surface active agent | 2.5 parts |
| Physiological saline solution | 97 parts |

The above ingredients were heated and mixed, and then sterilized to obtain an injection.

Formulation Example 4

| Compound (A) or (B) | 0.01 part |
|---|---|
| 0.5% Carboxymethylcellulose | 99.99 parts |

The former was suspended in the latter to obtain a suspension.

Formulation Example 5

| Compound (A) or (B) | 1 part |
|---|---|
| Polyethylene glycol 400 | 99 parts |

The above ingredients were mixed to dissolve the compound (A) or (B) to obtain a liquid preparation for painting.

Formulation Example 6

| Compound (A) or (B) | 2 parts |
|---|---|
| Polyethylene glycol 400 | 49 parts |
| Polyethylene glycol 4000 | 49 parts |

The above ingredients were mixed by heating to dissolve Compound (A) or (B), and the obtained mixture was cooled to obtain an ointment.

Formulation Example 7

| Compound (A) or (B) | 3 parts |
|---|---|
| 1,2-Propanediol | 5 parts |
| Glycerol stearate | 5 parts |
| Spermaceti | 5 parts |
| Isopropyl myristate | 10 parts |
| Polysorbate | 4 parts |

A mixture of the above ingredients was heated and cooled, and 68 parts of water was added thereto with stirring to obtain a cream.

Formulation Example 8

One part of Compound (A) or (B), 5 parts of benzyl alcohol, 30 parts of ethanol and 47 parts of propylene glycol were mixed to dissolve Compound (A) or (B). Then, an aqueous solution comprising 1 part of Hiviswako 104 (trademark, Wako Junyaku Co., Ltd.) and 15 parts of purified water to obtain a uniform solution was added to this solution. Next, 1 part of diisopropanolamine was added thereto with stirring to obtain a gel preparation.

Formulation Example 9

One part of Compound (A) or (B) was dissolved in 5 parts of benzyl alcohol and 5 parts of diethyl sebacate, and thereto were added 5 parts of cetyl alcohol, 6 parts of stearyl alcohol, 1 part of sorbitan monostearate and 8 parts of polyoxyethylene monostearate, followed by heating to 70° C. to dissolve them. To the resulting uniform solution kept at 70° C. was added a purified water heated to 70° C., followed by cooling with stirring to obtain a cream composition.

Test Example 1
In vitro Activity against *trichophyton* spp.:

Minimum inhibitory concentrations (MICs) were determined by the twofold macro-broth dilution method with Sabouraud's glucose broth which constituted with 1% bactopeptone and 4% glucose. To each tube containing 9.8 ml of the broth, 0.1 ml of each testing compound dissolved in DMSO and 0.1 ml of a conidial suspension ($1\times10^6$ conidia/ml) were added. The fungal growth was observed after incubation for 7 days at 27° C. The MIC was determined as the lowest drug concentration which prevented a visible fungal growth. The results are shown in Table 1.

TABLE 1

| | MIC ($\mu$g/ml) | | | | |
|---|---|---|---|---|---|
| Strain | Compound (A) | Compound (B) | Racemic Compound (A) | Racemic Compound (B) | TBF |
| A | | | | | |
| IFO 5466 | 0.02 | 0.02 | 0.04 | 0.04 | 0.02 |
| IFO 5809 | 0.005 | 0.005 | 0.01 | 0.02 | 0.01 |
| IFO 5810 | 0.005 | 0.005 | 0.01 | 0.01 | 0.005 |
| IFO 5811 | 0.02 | 0.01 | 0.04 | 0.04 | 0.01 |
| IFO 5929 | 0.01 | 0.01 | 0.02 | 0.02 | 0.01 |
| TIMM 1189 | 0.01 | 0.01 | 0.04 | 0.02 | 0.01 |
| TIMM 1814 | 0.02 | 0.02 | 0.04 | 0.04 | 0.01 |
| TIMM 1815 | 0.02 | 0.02 | 0.04 | 0.04 | 0.02 |
| TIMM 1817 | 0.02 | 0.01 | 0.04 | 0.02 | 0.01 |
| TIMM 2789 | 0.005 | 0.0025 | 0.01 | 0.01 | 0.0025 |
| B | | | | | |
| IFO 5467 | 0.0013 | 0.0025 | 0.005 | 0.005 | 0.005 |
| IFO 5807 | 0.0025 | 0.0025 | 0.01 | 0.01 | 0.005 |
| IFO 5808 | 0.0025 | 0.0025 | 0.01 | 0.01 | 0.005 |
| IFO 6203 | 0.0025 | 0.0013 | 0.005 | 0.005 | 0.0025 |
| IFO 6204 | 0.0025 | 0.0025 | 0.01 | 0.01 | 0.005 |
| IFO 9185 | 0.0013 | 0.0013 | 0.0025 | 0.0025 | 0.0025 |
| TIMM 1822 | 0.0013 | 0.00063 | 0.005 | 0.0025 | 0.0025 |
| TIMM 1823 | 0.0025 | 0.0013 | 0.01 | 0.05 | 0.0025 |
| TIMM 1824 | 0.0013 | 0.0013 | 0.005 | 0.005 | 0.0013 |
| TIMM 1830 | 0.00063 | 0.00063 | 0.0013 | 0.0013 | 0.00063 |

(Notes)
A: *Trichophyton mentagrophytes*
B: *Trichophyton rubrum*
TBF: (E)-N-(6,6-Dimethyl-2-hepten-4-ynyl)-N-methyl-1-naphthalenemethaneamine hydrochloride (general name: terbinafine)
Racemic Compounds (A) and (B) are racemic mixtures of Compounds (A) and (B), respectively.

Test Example 2
Therapeutic Efficacy on Experimental Tinea Pedis in Guinea Pigs with Compound (A):

Male Hartley guinea pigs (Japan SLC Inc.) weighing 400 to 620 g were used for the infection study. One side of a paper disc (1.5 mm thick×8 mm diameter) was covered with a piece of aluminum foil while the other side was free to carry the inoculum suspension. The disc was immersed with 50 $\mu$l of the inoculum suspension (*trichophyton mentagrophytes* TIMM 2789, $1\times10^8$ conidia/ml), and was then fixed on the planta pedis of animal feet with an adhesive elastic tape. The disc was removed on the seventh day postinfection. Each agent dissolved in PEG 400 (0.1 ml/locus) was topically applied to the whole soles of guinea pigs once a day for 3 consecutive days, starting on the 10th day postinfection. Five days after the last treatment, the skin tissue from each planta pedis and the corresponding tarsus of all animals was cut into small blocks (about 2×2 mm). Ten skin blocks obtained from each part of the foot were implanted on a Sabouraud's glucose agar plate containing antibiotics, and were cultured at 27° C. for 14 days. The skin blocks yielding fungal growth were regarded as culture-positive, and the foot (planta pedis plus tarsus) with more than one culture-positive skin block was considered fungus-positive. In addition, the intensity of infection was assessed by the scores based on the number of culture-positive skin blocks. Namely, +10, +9, +8, +7, +6, +5, +4, +3, +2, +1 or 0 was given as the score according to the corresponding number of culture-positive skin blocks out of ten skin blocks studied. Statistical analyses for the rate of fungus-positive feet and the average intensity of infection were assessed by Fisher's exact probably test and Mann-Whitney's U-test, respectively. The results are shown in Table 2.

TABLE 2

| | Fungus-positive rate The number of positive feet/The total | Average intensity of infection | |
|---|---|---|---|
| Test group | number of feet (%) | *Planta pedius* | Tarsus |
| 0.5% Compound (A) | 2/10 (20)[A,B] | +0.3[A,B] | 0[A,B] |
| 1% Compound (A) | 0/10 (0)[A,B,C] | 0[A,B] | 0[A,B] |
| 1% Racemic compound (A) | 4/10 (40)[A,B] | +0.6[A,B] | +0.2[A,B] |
| Untreated | 10/10 (100) | +7.7 | +5.4 |
| PEG 400 | 10/10 (100) | +7.9 | +4.8 |

(Notes)
A: $p < 0.01$ vs untreated control group
B: $p < 0.01$ vs PEG 400 treated control group
C: $p < 0.05$ vs 1% Racemic Compound (A) treated group The fungus-positive rate of the untreated group was 100% and fungi were detected from all of the infected feet. In terms of the average intensity of infection, a high value of +7.7 was obtained in the planta pedis, but it was +5.4 in the tarsus. Thus, this shows a tendency that the degree of infection in the tarsus was lower than in the planta pedis. Nearly the same results were obtained in the PEG 400 treated group and the curative effect by the solvent was not recognized. The 1% Racemic Compound (A) treated group showed a significant curative effect as compared with the untreated group and the PEG 400 treated group, but the fungus-positive rate was 40% and the average intensity of infection of the planta pedis and the tarsus was +0.6 and +0.2, respectively, and fungi were detected from four feet among the inoculated ten feet. In the 0.5% Compound (A) treated group, the fungus-positive rate was 20%, which shows that the effect of Compound (A) was twice that of 1% Racemic Compound (A), and in the 1% Compound (A) treated group, the remarkable effect that all of the infected feet were cure fungus-negative was obtained, namely, mycologically complete healing was attained.

As a result of the comparison between Compound (A) and Racemic Compound (A), it became clear that Compound (A) showed a curative effect markedly higher than Racemic Compound (A) at the same concentration and that when 0.5% Compound (A) and 1% Racemic Compound (A) which were the same in concentration in terms of active ingredient (A.I.) which was Compound (A) were compared, Compound (A) showed the higher effect more than twice that of 1% Racemic Compound (A). Considering MIC for T. mentagrophytes TIMM 2789 used for the test, it is clear that Compound (A) had in vitro antifungal activity of 4 times that of Racemic Compound (A), and this difference in antifungal action was reflected also in the curative test for the infection model in vivo.

Test Example 3
In Vitro Antifungal Activity Against Candida albicans:

MICs were determined by the twofold micro-broth dilution method with RPMI 1640 buffered with morphorinopropanesulfonic acid to a final molarity of 0.165M (pH 7.0). One hundred $\mu$l of a yeast cell suspension (1 to $5 \times 10^3$ cells/ml) and 100 $\mu$l of the compound-containing medium were pipetted into each well flat-bottomed microtiter plates. After incubation for 48 hours at 35° C., the turbidity of each well was measured at 630 nm. The MIC was determined as the lowest drug concentration which showed 80% inhibition of a control fungal growth (as measured in turbidity-increase). The results are shown in Table 3.

TABLE 3

| | MIC ($\mu$g/ml) | | | | | |
|---|---|---|---|---|---|---|
| Strain | Compound (A) | Compound (B) | Racemic Compound (A) | Racemic Compound (B) | TBF | FCZ |
| IFO 0197 | 0.0625 | 0.0625 | 0.25 | 0.125 | >32.0 | 0.25 |
| IFO 0579 | 0.0313 | 0.0313 | 0.0625 | 0.0625 | >32.0 | 0.125 |
| IFO 1269 | 0.0625 | 0.0625 | 0.125 | 0.0625 | 4.0 | 0.25 |
| IFO 1270 | 0.25 | 0.25 | 1.0 | 0.25 | >32.0 | 0.25 |
| IFO 1385 | 0.0625 | 0.0625 | 0.25 | 0.125 | >32.0 | 0.25 |
| IFO 1386 | 0.125 | 0.125 | 0.25 | 0.25 | >32.0 | 0.5 |
| TIMM 3163 | 4.0 | 16.0 | 16.0 | >32.0 | >32.0 | 16.0 |
| TIMM 3164 | 0.25 | 0.5 | 0.5 | 0.5 | >32.0 | 2.0 |
| TIMM 3165 | 2.0 | 2.0 | 4.0 | 4.0 | >32.0 | >32.0 |
| TIMM 3166 | 1.0 | 1.0 | 2.0 | 4.0 | >32.0 | 8.0 |

(Note) FCZ: 2-(2,4-Difluorophenyl)-1,3-bis(1H-1,2,4-triazol-1-yl)-2-propanol (general name: fluconazole)

Test Example 4
In Vitro Antifungal Activity of Compound (B) Against Aspergillus fumigatus:

MICs were determined by the twofold agar dilution method with casitone agar which constituted with 0.9% bactocasitone, 1% bacto-yeast extract, 2% glucose, 0.1% $KH_2PO_4$, 0.1% $Na_2HPO_4$, 1% $Na_3C_6H_5O_7$ and 1.6% agar. A loopful of each inoculum ($1 \times 10^6$ conidia/ml) was streaked onto the agar plate containing a compound, and a fungal growth was observed after incubation for 48 hours at 35° C. The MIC was determined as the lowest drug concentration which prevented a visible fungal growth. The results are shown in Table 4.

TABLE 4

| | MIC (μg/ml) | | | | | |
|---|---|---|---|---|---|---|
| Strain | Compound A | Compound B | Racemic Compound A | Racemic Compound B | TBZ | ITZ |
| TIMM 0063 | 0.00063 | 0.00063 | 0.0013 | 0.0013 | 1.28 | 0.04 |
| TIMM 0078 | 0.00063 | 0.00063 | 0.0013 | 0.0013 | 1.28 | 0.04 |
| TIMM 1728 | 0.0013 | ≦0.00031 | 0.0013 | 0.00063 | 1.28 | 0.08 |
| TIMM 1767 | 0.0013 | 0.00063 | 0.0025 | 0.0013 | 1.28 | 0.08 |

(Note) ITZ: (±)-1-sec-Butyl-4-[p-[4-[p-[[2R*,4S*]-2-(2,4-dichlorophenyl)-2-(1H-1,2,4-triazol-1-ylmethyl)-1,3-dioxolan-4-yl]methoxy]phenyl]-1-piperazinyl]phenyl-$\Delta^2$-1,2,4-triazolin-5-one (general name: itraconazol)

We claim:

1. R-(−)-(E)-[4-(2,4-Dichlorophenyl)-1,3-dithilan-2-ylidene]-1-imidazolylacetonitrile or a pharmaceutically acceptable salt thereof.

2. A pharmaceutical composition comprising as an active ingredient R-(−)-(E)-[4-(2,4-dichlorophenyl)-1,3-dithiolan-2-ylidene]-1-imidazolylacetonitrile, or a pharmaceutically acceptable salt thereof; together with a pharmaceutically acceptable carrier or diluent.

3. A process for producing R-(−)-(E)-[4-(2,4-dichlorophenyl)-1,3-dithiolan-2-ylidene]-1-imidazolylacetonitrile represented by formula (B):

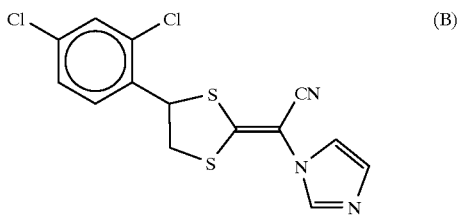

which comprises reacting an optically active glycol derivative represented by formula (II) with a dithiolate salt represented by formula (III):

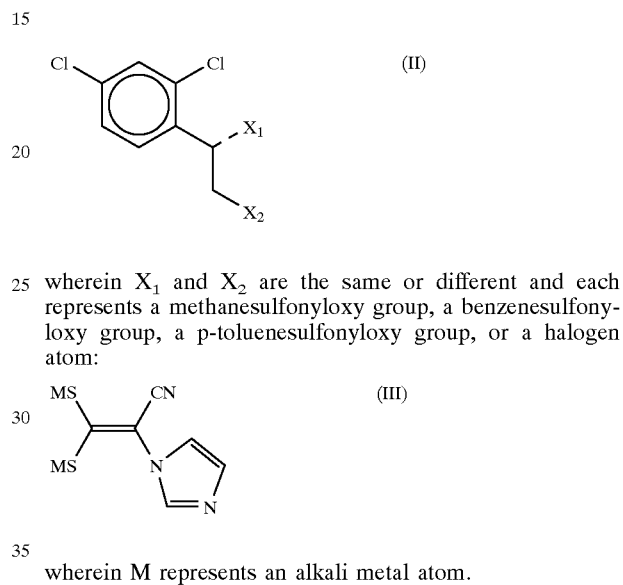

wherein $X_1$ and $X_2$ are the same or different and each represents a methanesulfonyloxy group, a benzenesulfonyloxy group, a p-toluenesulfonyloxy group, or a halogen atom:

wherein M represents an alkali metal atom.

4. A method for preventing or treating mycosis which comprises administrating to a human or animal in need of such prevention or treatment, a pharmaceutically effective amount of R-(−)-(E)-[4-(2,4-dichlorophenyl)-1,3-dithiolan-2-ylidene]-1-imidazolylacetonitrile, or a pharmaceutical acceptable salt thereof.

* * * * *